(12) United States Patent
Bruzzi

(10) Patent No.: US 7,685,894 B2
(45) Date of Patent: Mar. 30, 2010

(54) PROBE AND SYSTEM FOR EXTRACTING GASES FROM A PROCESS ENVIRONMENT

(76) Inventor: Domenico Bruzzi, Via Faldella 57, Crescentino (Vercelli) (IT) I-13044

( * ) Notice: Subject to any disclaimer, the term of this patent is extended or adjusted under 35 U.S.C. 154(b) by 293 days.

(21) Appl. No.: 10/594,656

(22) PCT Filed: Apr. 7, 2005

(86) PCT No.: PCT/IB2005/051145

§ 371 (c)(1),
(2), (4) Date: Sep. 27, 2006

(87) PCT Pub. No.: WO2005/098392

PCT Pub. Date: Oct. 20, 2005

(65) Prior Publication Data

US 2008/0229848 A1    Sep. 25, 2008

(30) Foreign Application Priority Data

Apr. 9, 2004   (IT) .............................. VC04A0002

(51) Int. Cl.
*G01N 1/00* (2006.01)
(52) U.S. Cl. .................................................. 73/864.33
(58) Field of Classification Search .............. 73/864.33, 73/23.31, 863.11, 863.12, 864.81, 863–432.1
See application file for complete search history.

(56) References Cited

U.S. PATENT DOCUMENTS 3,106,843 A * 10/1963 Luxl ........................ 73/863.12
3,220,385 A * 11/1965 Sellin .......................... 122/156
3,938,390 A * 2/1976 Grey ........................ 73/863.11
3,960,500 A   6/1976 Ross et al. ..................... 422/62
4,336,722 A * 6/1982 Schweitzer .............. 73/863.12
5,777,241 A * 7/1998 Evenson ................... 73/863.11

FOREIGN PATENT DOCUMENTS

| CA | 2 196 846      | 8/1998 |
| DE | 4430378 A1   * | 2/1996 |
| EP | 0 429 143      | 5/1991 |
| GB | 1445061 A    * | 8/1976 |
| JP | 11190686 A   * | 7/1999 |

* cited by examiner

*Primary Examiner*—Hezron Williams
*Assistant Examiner*—Tamiko D Bellamy
(74) *Attorney, Agent, or Firm*—Merchant & Gould P.C.

(57) ABSTRACT

A probe (S) for the extraction of gas from a process environment comprises a tubular element (2), which can be positioned within the process environment. This tubular element has at one end a gas aspiration opening (TS) and defines an internal cavity (CA) by which the interior of the process environment can be put into fluid communication with a gas take off system. The probe further includes a second tubular element (1) extending into the interior of the cavity of the first tubular element (2). This second tubular element has one end (UG) disposed at the aspiration opening end (that is to say the process environment side), formed in such a way as to inject the said accelerated gaseous fluid towards the aspiration opening of the first tubular element (2) and from there back to the process environment. Also envisaged is a system for the extraction of gas from a process environment which can be coupled to the probe, comprising a circuit (40, C) aspirating the gas from the process environment through the cavity (CA) of the first tubular element of the probe (2), and a circuit (50, C) for re-injecting the said gas into the same process environment through the second tubular element of the probe (1).

13 Claims, 4 Drawing Sheets

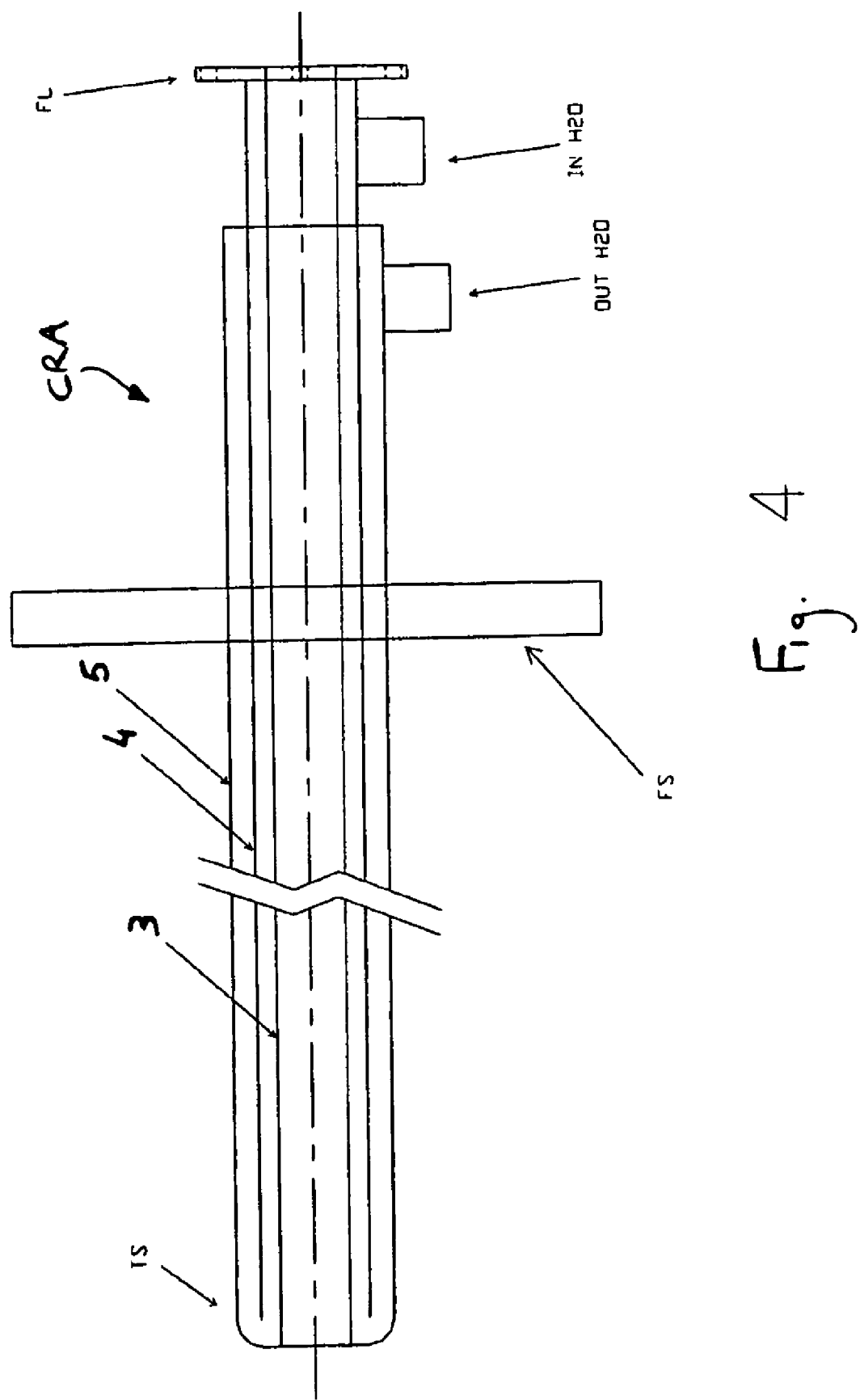

PROBE AND SYSTEM FOR EXTRACTING GASES FROM A PROCESS ENVIRONMENT

BACKGROUND OF THE INVENTION

The present invention relates in general to systems for the regulation and control of chemical processes which involve the production of gas, for example processes in cement furnaces.

Systems are known for the extraction of gases from a furnace, provided with probes to be mounted within the furnace, in which the gases extracted are conveyed to analyser devices.

For the extraction of the gases such systems utilise a small pump of low power and low pressure, in suction (through the probe). This implies treating the gases hot/moist, giving rise to corrosive acids which attack the couplings, the tubes and the various components involved in the flow of gas, aggravating the situation. For the purpose of avoiding the precipitation of condensate in the system (because it draws in hot/moist gas), it is necessary to heat the aspiration tube, the filter and the tube but with declining results (problems of packing, acids etc).

The probes further have serious problems of blockage of the gas aspiration tube, which make operation unreliable.

Moreover, in traditional probes the filtering of dust is achieved solely by the filter which is overloaded and becomes clogged. The cleaning of the probe is achieved by a washing cycle with compressed air (programmable) but often it is insufficient fully to restore it and, moreover, this introduces contamination into the gas to be analysed.

Because of these problems the values of the furnace gas analysis are approximate and irregular, leading to a misunderstanding of a correct management of the line, especially in the presence of alternative fuels. With these latter, even the best probes currently in commercial use show their limits. Only by meticulous and continuous surveillance and maintenance by man is it possible to obtain results, which even then are only just sufficient.

SUMMARY OF THE INVENTION

GB-A-1 445 061, U.S. Pat. No. 4,336,722, DE 44 30 378 A1, CA-A1-2 196 846 and U.S. Pat. No. 3,938,390 disclose systems for extracting a gaseous fluid to be analyzed from a process environment.

In particular, GB-A-1 445 061 discloses a system for extracting a gaseous fluid to be analyzed from a process environment, comprising
- a probe for extracting said gaseous fluid, comprising a first tubular element, which can be position within the interior of the process environment, the said first tubular element having at one end a gas aspiration opening and defining an internal cavity, and a second tubular element, the said second tubular element being operable to inject the said gaseous fluid into the interior of the cavity towards the said aspiration opening of the first tubular element and from there again into the process environment,
- aspiration means aspirating the gaseous fluid from the process environment through the cavity of the said first tubular element of the probe,
- take-off means connected to the said aspiration means for taking-off a fraction of the said gaseous fluid, the said take-off means by further connected to analyzer means for analysis of the said gaseous fluid, and
- re-injection means for re-injection the said gaseous fluid into the process environment through the second tubular element.

The system of GB-A-1 445 061 solves the problem of preventing the clogging of the prove only in a limited way.

One object of the invention is that providing a system for extracting a gaseous fluid to be a analyzed from process environment which is able to prevent or at least reduce the occurrence of clogging of the probe, that is to say to guarantee continuity of use without continual maintenance interventions (with improvements in the gas extraction system and continuity and reliability of the analysis).

This object is achieved according to the invention by a system for extracting a gaseous fluid to be analyzed from a process environment.

Another object of the invention is a method for extracting and re-injecting a gaseous fluid from and to a process environment.

Preferred embodiments of the system are defined in the dependant claims.

This system, by co-operating with the probe according to the invention, lowers the dust (filter less stressed), makes it possible to dry the gas (no clogging and no origination of acids) and is self cleaning without the aid of compressed air but by utilising the same process gas (continuity of analysis since it is not altered).

Its use makes it possible to extract combustion gases from a furnace so that they can be analysed by means of classical analyzers. It makes it possible to obtain reliable analysis of the combustion gases of the furnaces. Consequently, there is the possibility of optimising the control of the installation (reducing fuel consumption and improving the quality/quantity of the furnace product) and of monitoring/reducing atmospheric emissions.

It is applicable to any type of furnace (in any conditions of use; temperature, dust level, steam, acid etc) with any type of fuel (even alternative/waste disposal fuel) and any type of process material.

The reliability and continuity of the system makes it possible to utilize its output for automatic furnace management (not having compressed air washing which gives rise to O2 peaks). The capacity of the compressor is high, therefore the response is faster than in usual systems, and possible microlosses have no influence. Consequently a more reliable analysis is achieved.

The probe has been designed for cement furnaces but can be used in process environments in industries of different type; steelworks, thermo-electric plants, chemical/petrochemical industries, carbon grinding and storage, incinerators, explosive powder storage silos, that is to say in all those sectors where it is required to extract gas for subsequent analysis (furnaces, silos, chimneys, pipework etc).

The salient characteristic of the probe and the system according to the invention is the reduced necessity for maintenance. This is achieved by avoiding aspiration of dust/condensate, and thanks to the violent and continuous spraying of compressed gas ensured by the compressor.

The filter has a long life since it is self-cleaning by means of the powerful counter current flow of gas during the rapid discharge for probe cleaning.

Moreover a reduction of dry dust is achieved by using the compressed gas from the furnace and without a water spray. There is moreover a drying of the gas with consequent reduction of acids. The system is self-cleaning with a continuous cycle, again by the effect of the compressed gas, and therefore does not require the washing cycle with compressed air which would falsify the gas analysis (by polluting it) but by using the gas from the furnace. This avoids having to use a large number of control panels for the treatment of the gas (with filters, antacids, bubbling chambers etc), control panels for solenoid valves and various dedicated electrical control panels (with PLC). This leads to a reduction of the associated problems and costs.

The probe is easy to install in a short time, not requiring a great deal of work for adaptation of the existing system to be able to connect it. Moreover, it does not require a great deal of care in research for the optimum position in the furnace (the minimum dust point etc.)

For use at high temperatures the probe is water-cooled. It has an anti-condensate interspace for decoupling the hot zone (gas circuit) from the cold zone (cooling water jacket), permitting the gas extracted to maintain its temperature. This arrangement avoids the formation of condensate in the inner wall of the aspiration tube, thereby minimising clogging of the dust. The two chambers for gas and cooling can be separated because they are coupled with flanges. This makes is possible to remove only the gas circuit from the furnace (for a possible inspection and cleaning, even with the furnace in operation) leaving only the cooling system fixed to the furnace.

The probe is easy to install in a short time, not requiring a great deal of work for adaptation of the existing system to be able to connect it. Moreover, it does not require a great deal of care in research for the optimum positioning in the furnace (the minimum dust point etc).

BRIEF DESCRIPTION OF THE DRAWINGS

A preferred but non-limitative example of the invention will now be described making reference to the attached drawings, in which;

FIG. 4 is a schematic side view of the cooling jacket of the probe of FIG. 2.

DETAILED DESCRIPTION OF THE PREFERRED EMBODIMENT(S)

Figure 1:
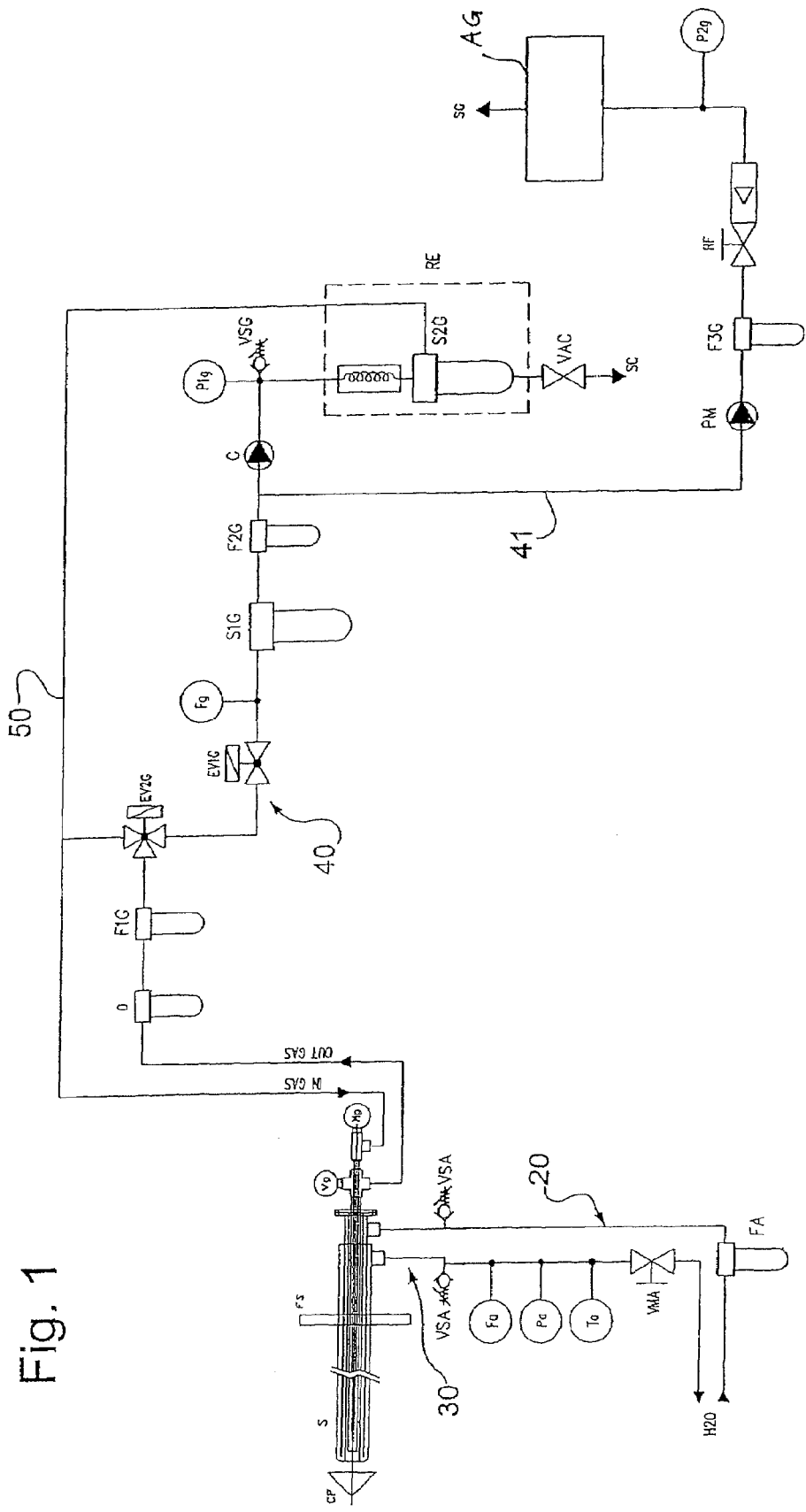
FIG. 1 is a general diagram of a system for the extraction of burnt gases from a furnace according to the invention.

Making reference to FIG. 1, a system for the extraction of gas from a process environment, for example a furnace (not illustrated) comprises a probe S, a compressor C, a piping 20 for supply of cooling water to the probe S and a piping 30 for the discharge of this water from the probe S, a piping 40 for aspiration of gas from the probe S and a piping 50 for the re-injection of the gas to the probe S/process environment.

The system is supplied with an electric voltage for the compressor C and solenoid valves EV1G, EV2G, a fluid, for example water, for cooling the probe S, and a compressed fluid, for example air, for the solenoid valve actuators EV1G, EV2G. Alternatively, a low temperature refrigerator with closed circuit water could be used for the cooling system.

Figure 3:
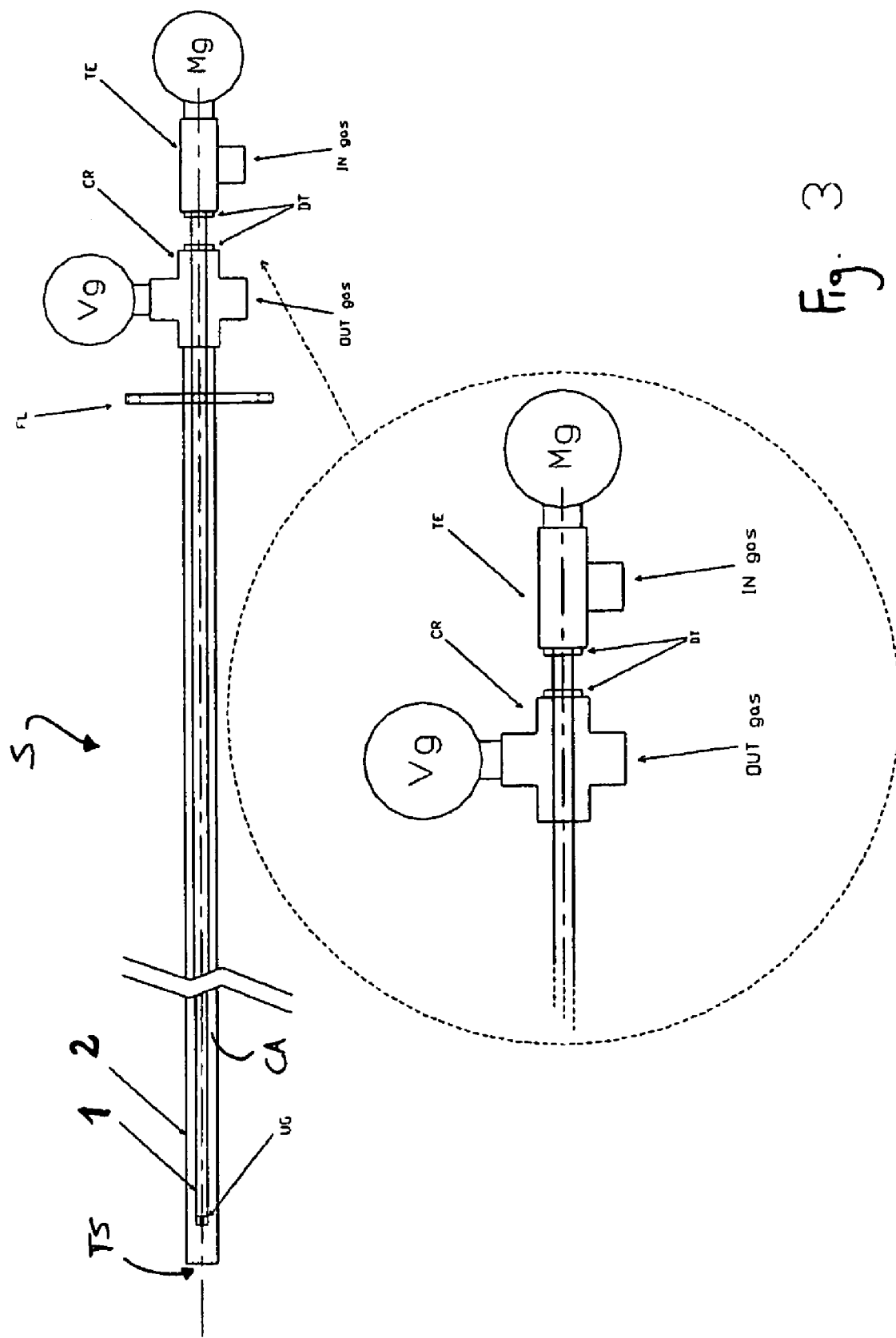
FIG. 3 is a schematic side view of a probe of FIG. 2 without the cooling jacket.

With reference to FIG. 3, the probe S in its essential form comprises two concentric tubes 1 and 2, for example in AISI304 steel, but it is possible to utilise material more suitable to high temperatures and resistant to acid corrosion. The outer tube 2 is dedicated to the aspiration of gas, the inner tube 1 is the gas delivery. This probe S is usable in low temperature environments. To utilise it with high temperatures it is necessary to provide it with a water-cooling jacket (illustrated in FIG. 4).

Figure 2:
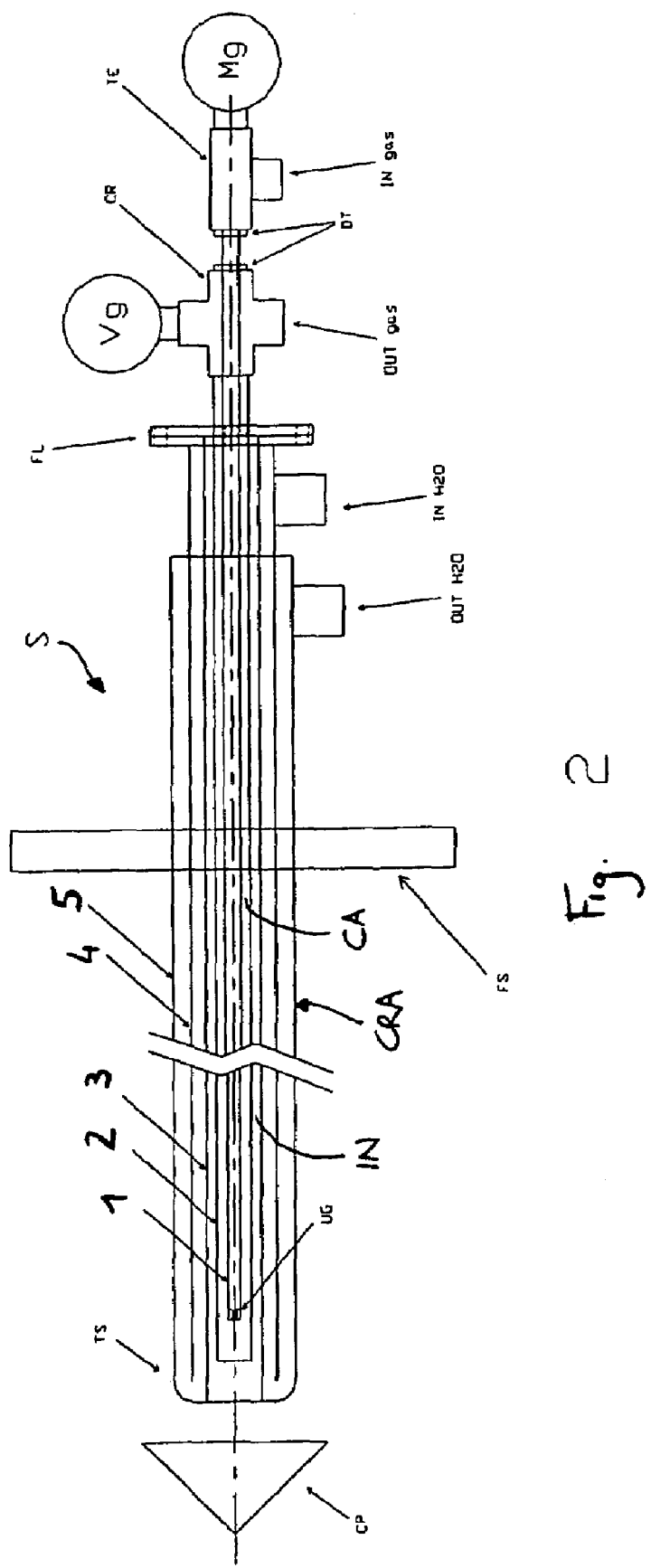
FIG. 2 is a schematic side view of a probe for extraction of burnt gases from a furnace, according to the invention.

In FIG. 2 the probe S is shown provided with a gas circulation chamber and a water-cooling jacket CRA. This version (with water cooling) is for high temperatures and comprises five concentric tubes 1, 2, 3, 4, 5. The probe S is fitted to and fixed in the wall of the furnace by means of a support flange FS. The probe head TS is fitted with a protection cone CP acting as a first barrier against the ingress of impurities into the probe.

The three outermost tubes 3, 4, 5 constitute the cooling chamber CRA through which flows water (fixed solidly to the furnace by means of the flange FS to permit its fitting and fixing). The space between the innermost tube 3 and the intermediate tube 4 of the jacket CRA is connected to the water supply piping 20 by means of a water filter FA for cooling water, and the space between the intermediate tube 4 and the outermost tube 5 of the jacket CRA is connected to the water discharge piping 30 by means of a manual valve VMA for regulation of the rate of flow of cooling water. The said spaces are fluidly connected at the head TS of the probe. Upstream of the supply piping 20 and downstream of the discharge piping 30 are disposed respective coolant water relief valves VSA. In the discharge piping 30 are, moreover, disposed a sensor Ta for control of the water temperature, a sensor Pa for control of the water pressure and a sensor Fa for control of the water flow.

The two innermost tubes 1 and 2 constitute the gas extraction probe true and proper (fitted and coupled to the coolant jacket by means of flange FL to allow its removal in a simple and rapid manner, even with the installation in operation see FIGS. 2 and 3).

The coupling of the two chambers (gas and cooling, that is to say the second and third tube 2, 3, from the inside working outwardly), gives rise to an interspace IN, blind at the probe bottom (outer furnace side) and open at the head TS (inner furnace size) that is to say it is licked by the gas. This avoids the formation of condensation within the gas aspiration tube 2 (second tube) and makes it possible for the gas withdrawn not to be excessively cooled. The gas is aspirated into the chamber CA constituted by the first and second tube 1, 2 and injected again into the interior of the furnace through of the concentric central tube (first tube 1), by means of a compressor C. The furnace side end UG of the central tube is throttled so that the ejected gas is compressed. Preferably, this end has a nozzle. Alternatively, the same central tube 1 can be realized as a capillary tube for injection the gas towards the probe head TS. In this way the gas acquires a certain pressure and kinetic energy, constituting a barrier against dust and effecting cleaning of the probe head TS. In substance the gas is aspirated through the piping 40 and returned to the furnace with an adequate pressure and velocity through the piping 50, by means of the compressor C. In the gas aspiration and delivery circuit 40, 50 (furnace-compressor C-furnace) there is fitted a branch 41 which delivers a small percentage of fluid to be analysed to traditional analyzers AG by means of a pump PM with a take off upstream of the compressor C. The high flow rate of the circulating fluid guarantees short response times which benefit the management of the furnace. Upstream of the analyzers are disposed a regulator RF for the flow of gas to the analyzers and a sensor P2g for control of the pressure of the gas to the analyzers. These analyzers are moreover protected by a filter F3G, which acts as an anti-acid/condensate. Downstream of the analyzers is disposed a gas discharge SG exiting from the analyzers.

Before reaching the compressor C and the pump PM the gas is suitably filtered by upstream filters F1G and F2G in the aspiration piping 40. The filter F1G is connected to a dust decanter D to reduce the possible dust present in the circuit.

A sensor P1g for control of the gas pressure of the compressor and a valve VSG for gas overpressure of the compressor C are connected to the delivery of the compressor C.

There are also two reservoirs S1G (depressurized) and S2G (pressurized) in the system, on the aspiration and delivery sides of the compressor C respectively. These perform the function of collecting the condensate and stabilising the pressure/depression of the compressor. In particular, the reservoir S2G forms part of a refrigerator/dryer RE for reducing the condensate. Downstream of the reservoir S2G is connected an automatic condensate discharge valve VAC arranged to discharge the condensate SC. The reservoirs are also furnished with two timing solenoid valves EV1G and EV2G activating the respective servo-valves in a cyclic manner for times which can be set, depending on the requirements. The solenoid valve EV1G is a two-way valve mounted between the depressurized reservoir S1G and the aspiration of the probe S, and has the function of stopping the aspiration from the probe S so that the thrust of its delivery is reinforced to improve the cleaning of the probe head. Downstream of the solenoid valve EV1G is disposed a sensor Fg for control of the flow of gas to the compressor C. The three-way solenoid valve EV2G mounted upstream of the preceding one, has the function of violently discharging, with a full jet, the quantity of fluid in the pressure reservoir S2G, towards the aspiration tube 2. This enormous quantity of fluid flows at high velocity in the opposite direction from the normal flow, sweeping towards the furnace interior any possible deposits of material, thus effecting counter-current (back-washing) cleaning.

To monitor the good operation and to obtain an indication if it is becoming clogged, a vacuometer Vg is mounted on board the probe S on the aspiration tube 2, and a manometer Mg is mounted on the delivery tube 1. In particular, the vacuometer Vg is mounted on a cruciform connector CR, and the manometer Mg is mounted on a T-connector TE. The connectors CR, TE and nuts DT (with washers for sealing the gas in a gas-tight manner) also serve to hold the two tubes together. This arrangement makes it possible to make the central gas delivery tube 1 slidable with respect to the aspiration tube 2 for an optimum adjustment of the device.

The type of probe proposed makes it possible to have dry dust exclusion, gas drying and head cleaning in a continuous manner, avoiding packing of material. The analysis of the aspirated gas is continuous without interruptions (not deviated even for an instant) since there is no necessity for the cleaning cycle with compressed air (which gives rise to O2 peaks). This is achieved by utilising the compressor which makes the same gas re-circulate in the furnace; it aspirates and throws the gas back into the furnace, with a discrete pressure and kinetic energy, by means of the throttling of the nozzle positioned at the internal extremity of the delivery tube. Since the said tube is concentric with the aspiration tube, it creates a dust-filtering barrier as well as keeping the head clean. This, likewise, permits a sufficient drying of the aspirated gas. The cold and dried gas cleaned of dust does not give rise to condensation or acids, and does not leads to packing. The dust and condensate are cut out from the beginning and returned to the furnace, avoiding transporting them along the analysis installation. This is of benefit to the tubing, the connectors, the compressor, the pump, the analyzers, and the control and security sensors, and will result in a greater efficiency and duration of these. Moreover it is possible to make these of more economic commercial type and it is not necessary for them to be of the more expensive anti-acid type. The probe and the system according to the invention reduce dust (less stressed filter), dry the gas (no accretion and no origination of acids) and the probe is self-cleaning without the aid of compressed air but by utilising the same process gas (continuity of analysis since it is not altered).

In other words, with the compressor and the branching principle one obtains; dust-free and dried gas (by the barrier effect) and self-cleaning head without necessary for the compressed air washing cycle (by means of a continuous cycle interruption and alteration of the analysis gas.)

The strong point of this probe is the compressor central-tube which permits the gas to re-circulated to the furnace with a certain pressure and kinetic energy. Naturally, in place of the compressor it is possible to utilise another type of continuous cycle machine.

The invention claimed is:

1. A system for extracting a gaseous fluid to be analyzed from a process environment, comprising:
    a probe for extracting said gaseous fluid, the probe comprising:
    a first tubular element, which can be positioned within the interior of the process environment, the first tubular element having at one end a gas aspiration opening and defining an internal cavity, and
    a second tubular element extending within the cavity of the first tubular element, the second tubular element being operable to inject the gaseous fluid into the interior cavity towards the aspiration opening of the first tubular element, and into the process environment;
    aspiration means for aspirating the gaseous fluid from the process environment through the cavity of the first tubular element of the probe,
    take off means connected to the aspiration means for taking off a fraction of the gaseous fluid, the take off means being further connected to an analyzer; and
    re-injection means for re-injecting the gaseous fluid into the process environment through the second tubular element,
    a compressor having an aspiration side and a delivery side, wherein said aspiration means and the re-injection means share the compressor;
    wherein the first tubular element is in fluid communication with a control valve, the control valve being selectively operable to fluidly connect said first tubular element with one of the aspiration side or said delivery side of the compressor; and
    wherein the second tubular element is in fluid communication with the delivery side of said compressor through a reservoir, the second tubular element being throttled in such a way to accelerate the gaseous fluid flowing through it and, at the same time, to allow an accumulation of the gaseous fluid upstream within said reservoir,
    wherein in an aspiration condition, the gaseous fluid is aspirated through the first tubular element and is partially re-injected through the second tubular element and partially accumulated by the reservoir, and in a back washing condition, the accumulated gaseous fluid is released by the reservoir through the first tubular element by selective activation of the control valve.

2. A system according to claim 1, wherein the end of the second tubular element disposed on a process environment side of the aspiration opening, is provided with a nozzle.

3. A system according to claim 1, in which the first and second tubular element are coaxial.

4. A system according to claim 3, further comprising connector elements, pierced nuts and gas tight seals operable to assemble the first and second tubular element and to render the second tubular element slidable with respect to the first tubular element.

5. A system according to claim 1, further comprising a cooling jacket disposed around the first tubular element.

6. A system according to claim 5, wherein the cooling jacket is disposed in such a way as to define an inter space interposed between the jacket and the first tubular element.

7. A system according to claim 5, wherein the cooling jacket is assembled in a separable manner from the first tubular element of the probe.

8. A system according to claim 5, wherein the cooling jacket is connected in fluid communication with a low temperature refrigerator with a closed fluid circuit.

9. A system according to claim 1, further comprising a shielding element disposed in proximity to the aspiration opening.

10. A system according to claim 1, further comprising decanter means and drying means disposed downstream of the probe in such a way as further to reduce the dust and the condensate in the gas.

11. A system for extracting a gaseous fluid to be analyzed from a process environment, comprising:

a probe for extracting said gaseous fluid, comprising a first tubular element, which can be positioned within the interior of the process environment, the first tubular element having at one end a gas aspiration opening and defining an internal cavity, and a second tubular element extending within the cavity of the first tubular element, the second tubular element being operable to inject the gaseous fluid into the interior cavity towards the aspiration opening of the first tubular element and from there again into the process environment;

aspiration means for aspirating the gaseous fluid from the process environment through the cavity of the first tubular element of the probe;

take off means connected to the aspiration means for taking off a fraction of the gaseous fluid, the take off means being further connected to analyzer means;

re-injection means for re-injecting the gaseous fluid into the process environment through the second tubular element; and a vacuometer connected to the first tubular element of the probe and a manometer connected to the second tubular element of the probe for monitoring the operation conditions of the probe;

wherein said aspiration means and the re-injection means share compressor means, said compressor means having an aspiration side and a delivery side, wherein the first tubular element is fluidly connected to control valve means operable to fluidly connect said first tubular element selectively with one of the aspiration side and said delivery side of the compressor means; and wherein the second tubular element is disposed in fluid communication with the delivery side of said compressor means through a reservoir, the second tubular element being throttled in such a way to accelerate the gaseous fluid flowing through it and, at the same time, to allow an accumulation of the gaseous fluid upstream within said reservoir;

wherein in an aspiration condition, the gaseous fluid is aspirated through the first tubular element and is partially re-injected through the second tubular element and partially accumulated by the reservoir, and in a back washing condition, the gaseous fluid is released by the reservoir through the first tubular element by activation of the control valve means.

12. A method for extracting and re-injecting a gaseous fluid from and to a process environment with a probe for extracting said gaseous fluid, the probe comprising a first tubular element positionable within the interior of the process environment, the first tubular element having at one end a gas aspiration opening and defining an internal cavity; and a second tubular element extending within the cavity of the first tubular element, the second tubular element being operable to inject the gaseous fluid into the interior of the cavity towards the aspiration opening of the first tubular element and into the process environment, the method comprising:

aspirating the gaseous fluid from the process environment through the cavity of the first tubular element of the probe, taking off a fraction of the gaseous fluid for analyzing the gaseous fluid, re-injecting a first portion of the gaseous fluid into the process environment through the second tubular element of the probe, accumulating a second portion of the gaseous fluid;

performing back washing, wherein the accumulated gaseous fluid is released into the process environment through the first tubular element.

13. A method to claim 12, wherein the back washing step is performed cyclically.

* * * * *